(12) United States Patent
Siegenthaler

(10) Patent No.: US 11,793,993 B2
(45) Date of Patent: Oct. 24, 2023

(54) OPEN ELECTRIC PUMP

(71) Applicant: Michael Siegenthaler, Potomac, MD (US)

(72) Inventor: Michael Siegenthaler, Potomac, MD (US)

( * ) Notice: Subject to any disclaimer, the term of this patent is extended or adjusted under 35 U.S.C. 154(b) by 0 days.

(21) Appl. No.: 16/526,521

(22) Filed: Jul. 30, 2019

(65) Prior Publication Data

US 2020/0030508 A1    Jan. 30, 2020

Related U.S. Application Data

(60) Provisional application No. 62/711,856, filed on Jul. 30, 2018.

(51) Int. Cl.
*A61M 60/422* (2021.01)
*A61M 60/419* (2021.01)
*A61M 60/13* (2021.01)
*A61M 60/216* (2021.01)
*A61M 60/538* (2021.01)

(52) U.S. Cl.
CPC .......... *A61M 60/419* (2021.01); *A61M 60/13* (2021.01); *A61M 60/216* (2021.01); *A61M 60/422* (2021.01); *A61M 60/538* (2021.01); *A61M 2210/12* (2013.01)

(58) Field of Classification Search
CPC .. A61M 1/1036; A61M 1/125; A61M 60/135; A61M 60/857; A61M 60/00
See application file for complete search history.

(56) References Cited

U.S. PATENT DOCUMENTS

| | | | | |
|---|---|---|---|---|
| 6,201,329 B1* | 3/2001 | Chen | ..................... | A61M 60/82 417/423.1 |
| 8,690,749 B1* | 4/2014 | Nunez | ................. | A61M 60/205 600/16 |
| 9,945,418 B1* | 4/2018 | Allaire | ................ | F16C 32/0465 |
| 2006/0014999 A1* | 1/2006 | Heilman | ............. | A61M 1/1041 600/16 |
| 2011/0152999 A1* | 6/2011 | Hastings | ............... | A61M 60/40 623/1.15 |
| 2013/0138205 A1* | 5/2013 | Kushwaha | .......... | A61M 1/1087 623/1.26 |

(Continued)

FOREIGN PATENT DOCUMENTS

DE    10 2005 045597 A1    4/2007

OTHER PUBLICATIONS

International Search Report and Written Opinion dated Sep. 30, 2019 in PCT/US2019/044164, 12 pages.

(Continued)

*Primary Examiner* — Rex R Holmes
*Assistant Examiner* — Jennifer L Ghand
(74) *Attorney, Agent, or Firm* — XSENSUS LLP

(57) ABSTRACT

An implantable pump is configured to be implanted in series with blood flow from a heart. The pump includes a frame configured to be implanted within the natural blood flow of the heart such as a ventricular outflow tract an outlet valve of the heart, and a central axle configured to be affixed within the frame parallel to the blood flow. The pump also includes a rotor attached to the central axle and configured to rotate in order to pump blood, and at least two electromagnetic coils configured to be energized in order to cause the rotor to rotate.

8 Claims, 5 Drawing Sheets

(56) References Cited

U.S. PATENT DOCUMENTS

| | | | |
|---|---|---|---|
| 2014/0064987 A1 | 3/2014 | Cox, Jr. et al. | |
| 2014/0084759 A1* | 3/2014 | Takeuchi | B60L 3/0061 |
| | | | 310/68 B |
| 2014/0330069 A1* | 11/2014 | Hastings | A61M 1/1029 |
| | | | 600/16 |
| 2015/0141739 A1 | 5/2015 | Hsu et al. | |
| 2016/0089482 A1* | 3/2016 | Siegenthaler | A61N 1/057 |
| | | | 600/16 |
| 2016/0235898 A1* | 8/2016 | Yanai | A61M 60/818 |
| 2017/0021070 A1* | 1/2017 | Petersen | A61M 60/825 |
| 2017/0216507 A1* | 8/2017 | Kushwaha | A61M 60/871 |
| 2018/0326132 A1* | 11/2018 | Maimon | A61M 1/106 |
| 2020/0405926 A1* | 12/2020 | Alexander | A61M 60/408 |

OTHER PUBLICATIONS

Extended European Search Report dated Jun. 15, 2022 in European Application No. 19843389.8.

* cited by examiner

OPEN ELECTRIC PUMP

CROSS-REFERENCE TO RELATED APPLICATIONS

This application claims the benefit of priority of the filing date of provisional application No. 62/711,856, the entire contents of which are incorporated herein by reference.

BACKGROUND

Field

The present disclosure is directed to open electric pumps used to pump fluids. Specifically, the present disclosure describes an open electric pump that may be implanted in a failing heart to assist in the pumping of blood.

Description of the Related Art

Heart failure patients have failing hearts that do not adequately pump blood through the patient's circulatory system. Therefore, circulatory assist devices have been developed in order to aid a failing heart to pump blood. Such devices can include rotary axial flow pumps, or centrifugal pumps, that have rotors which pumps blood by spinning. These conventional pumps also include casings that surround the rotor with very small tolerances between the rotor and the casing wall. This "closed" design results in severe resistance to blood flow if the motor of the conventional pump stops pumping, which can occur if an associated battery pack becomes drained or if the conventional pump itself malfunctions.

To maintain circulation if the pump stops pumping, the conventional pump must be used in parallel to the natural blood flow of the heart, usually from the apex of the left ventricle to the ascending or descending aorta. Other parallel pump-configurations from a main pumping chamber or a pre-chamber to the aorta or pulmonary artery are also being used for left or right heart support. This parallel configuration allows the natural heart to eject and support circulation even if the pump is temporarily stopped. Implanting a conventional pump in series with the blood flow from the heart, such as in the left ventricle outflow tract or within an outflow valve of a main pumping chamber, can lead to catastrophic circulatory collapse if the conventional pump stops pumping, such as during a battery exchange, an inadvertent disconnection of the battery, or pump malfunction. This is because the closed design of conventional pumps allows very little blood to pass through them when the pump is stopped.

Conventional pumps also include coils that generate heat, which is transferred to the surrounding tissue and blood by the casing. This can case the blood and surrounding tissue to warm to the point of causing damage to blood proteins and other cellular blood components, possibly leading to clotting and a thromboembolism.

Thus, there is a need for a new pump design that is able to be implanted in series with the blood flow of the heart without causing significant resistance to blood flow if the pump stops, and that minimizes trauma to the blood and surrounding tissues and minimizes heat transfer to the surrounding tissues.

SUMMARY

The present disclosure is directed to a pump that has an "open" design to allow placement of the pump in series with blood flow from the heart. The open design of the pump also allows for a larger, more efficient rotor that pumps blood effectively at lower rotor speeds, resulting in less shear forces on the blood and its cellular components and therefore in less trauma. The open design of the pump greatly reduces resistance to blood flow in the event of a pump stoppage, minimizing the risk of circulatory collapse. Thus, the inventive pump described herein may be placed in, for example, the left or right ventricular outflow tract or within the position of an outflow valve of the right or left ventricle without any of the negative effects of conventional pumps.

The open design further provides for better heat exchange and potentially less blood trauma than conventional pumps due to the larger surface area exposed to the blood. In the pump, a much larger portion of the surface of the electromagnetic coils is in contact with the blood stream that in conventional pumps. This allows for a better heatsink function and less warming of the blood components, and reduces the likelihood of thromboembolic complications. The inventive open pump can also be configured so that endovascular/minimally invasive placement from within the blood stream is possible.

Specifically, in one aspect of the present disclosure, an implantable pump is configured to be implanted in series with blood flow from a heart. The pump includes a frame configured to be implanted in a ventricular outflow tract of the heart, and a central axle configured to be affixed within the frame parallel to the blood flow. The pump also includes a rotor attached to the central axle and configured to rotate in order to pump blood, and at least two electromagnetic coils configured to be energized in order to cause the rotor to rotate.

The timing of the electrical pulses to propel the pump rotor are based either on hall sensors or back electromagnetic pulse sensing (back EMP sensing) from the rotating magnets passing the coils. The pump is controlled by an electromechanical or electronic external control unit (not shown in pictures) which has the ability to adjust the pump rotary speed by manual control and also can have automatically adjustable variable pump speed features that adjust the rotary speed based on patient sensor input, such as the patient's heart rate, with a sensor for the electrical activity of the patient's heart (such as in an electrocardiogram) or with motion sensors detecting the degree of physical activity of the patient or detecting the respiratory rate and the body position of the patient.

The pump rotor and frame are made of biocompatible materials such as stainless steel, metal alloys such as titanium alloys such as Nitinol or other metal alloys, the bearings are made of materials such as ceramics, sapphire or ruby or metal or metal alloys. The rotor can be made of magnetic metals or metal alloys. The electrical coils of the pump are made of materials such as metal wire, such as copper or gold wire or any suitable metal or metal alloy wire and are encased in a water proof casing made of either a metal, a metal alloy or a polymer. The pump also uses polymers to insulate wires and wire connections.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
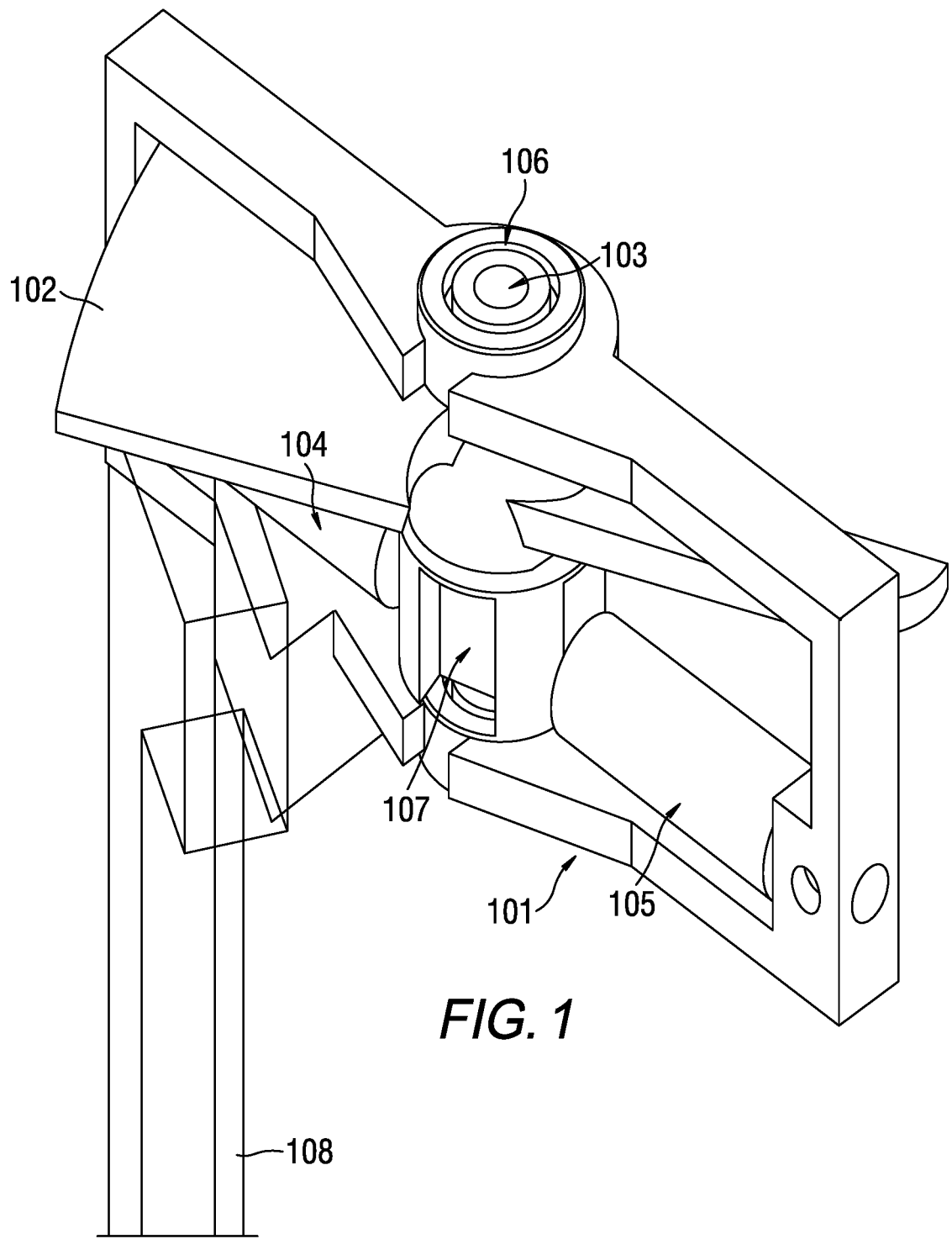
FIG. 1 is an open pump according to exemplary aspects of the present disclosure.

Referring now to the drawings, wherein like reference numerals designate identical or corresponding parts throughout the several views, FIG. 1 is an open pump according to exemplary aspects of the present disclosure. As illustrated in FIG. 1, the pump includes a frame 101 which holds a central axle 103 onto which a rotor 102 is mounted. Also attached between the central axle 103 and the frame are two electromagnetic coils 104 and 105, which cause the rotor 102 to turn when energized. The coils 104 and 105 are arranged radially or slightly "off-center" within the blood channel. In order to correctly time the signals provided to the electromagnetic coils 104 and 105, a Hall sensor is used or backward electromagnetic pulse sensing (EMP pulse sensing) is used. The pump also includes an opening 107 for insertion of one or more magnets that are used to cause the rotor 102 to rotate, and has a power cable 108 attached to the coils 104, 15 in order to provide power to those coils. The open pump does not include a casing, and is instead supported by the frame 101, thus minimizing resistance to blood flow.

FIG. 1 also illustrates that the frame 101 holds the central axle 103 in openings that receive a bushing 106, or similar retention device. The bushing 106 may be a pressure fit, and may be machined to have a recess around its outer circumference in order to fit within the opening in the frame 101. The bushing may also include a bearing, bearing assembly, or a pencil-point bearing, in order to allow the central axle 103 to spin freely with minimal resistance. Of course, other bushing and bearing designs are possible without departing from the scope of the present disclosure.

Though FIG. 1 illustrates the central axle 103 held by bushings 106 at either side of the frame 101, the bushings 106 may be omitted and the central axle 103 may be directly held by the frame 101 without any other structure. To prevent the central axle 103 from working itself free of the frame 101, a cotter pin or similar structure may be used. The holes in the frame 101 that hold the central axle 103 may also be "blind" holes that do not extend the entire thickness of the frame material in order to retain the central axle 103 in place. One of ordinary skill would recognize that other ways of rotatably affixing the central axle 103 to the frame 101 are possible without departing from the present disclosure.

Figure 2:
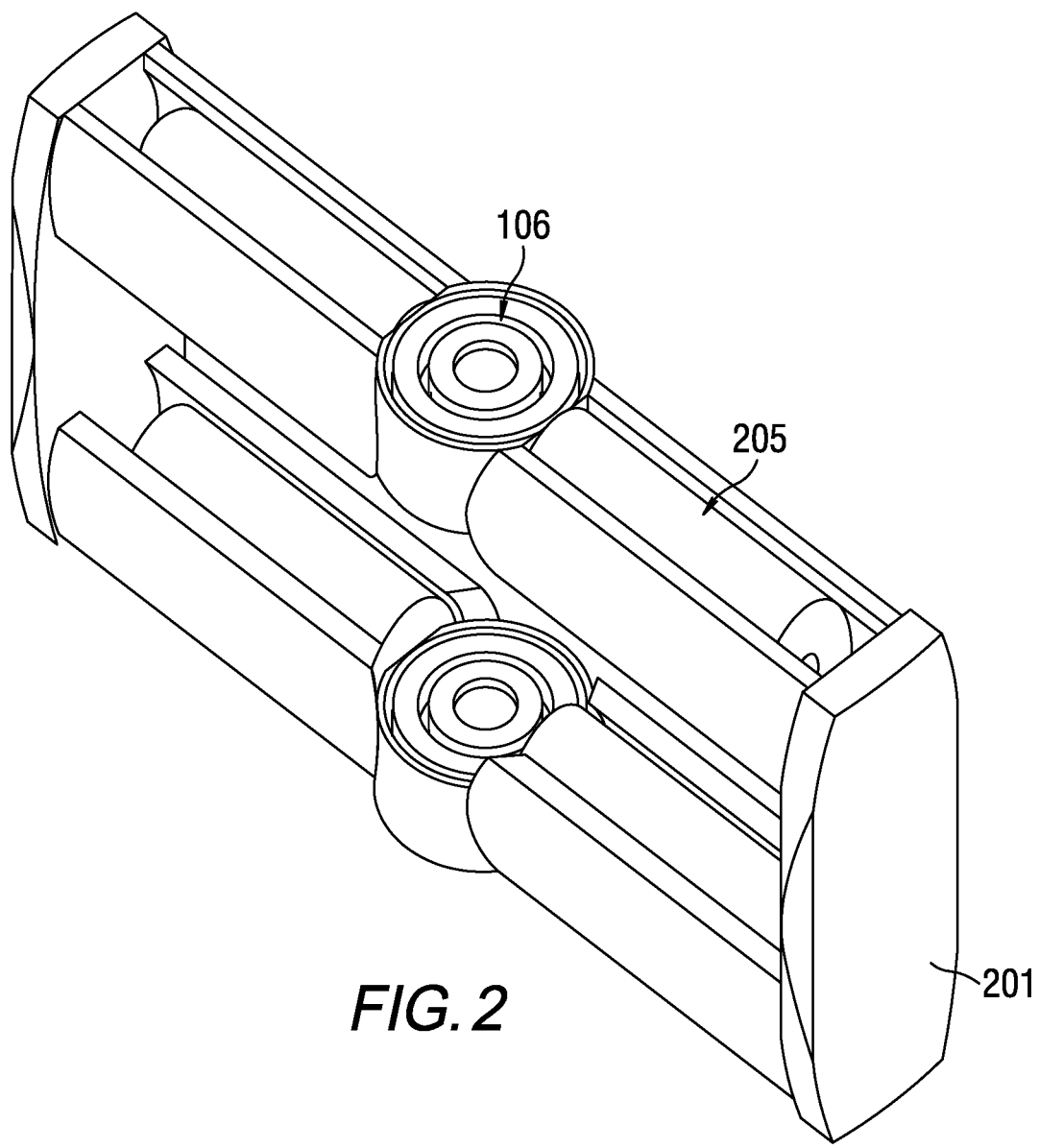
FIG. 2 is another perspective view of an open pump according to exemplary aspects of the present disclosure.

FIG. 2 is a perspective view of an open pump according to exemplary aspects of the present disclosure. In FIG. 2, the rotor is omitted for clarity. The frame 201 of FIG. 2 includes recesses in which coils 205 are placed. As can be seen two sets of opposing electromagnetic coils 205 are situated radially in the frame 201. They can also have a slightly "off-center" configuration to allow rotation of the pump in only one direction. The bushings 106 hold the central axle 3 (not shown) on which the rotor may be installed. Using a pair of electromagnetic coils allows for timing of the electrical pulses to the coils with back-electromagnetic pulse sensing, thus eliminating the need for a Hall sensor. Also, this configuration allows for a more powerful motor, which may be useful due to size constraints required for a minimally invasive placement of the pump. This set up with 4 or more magnets facilitates the use of EMP back sensing to time the pump as the pump can be propelled by one pair of magnets while the other pair is set for short periods of time in a sensing mode.

Figure 3:
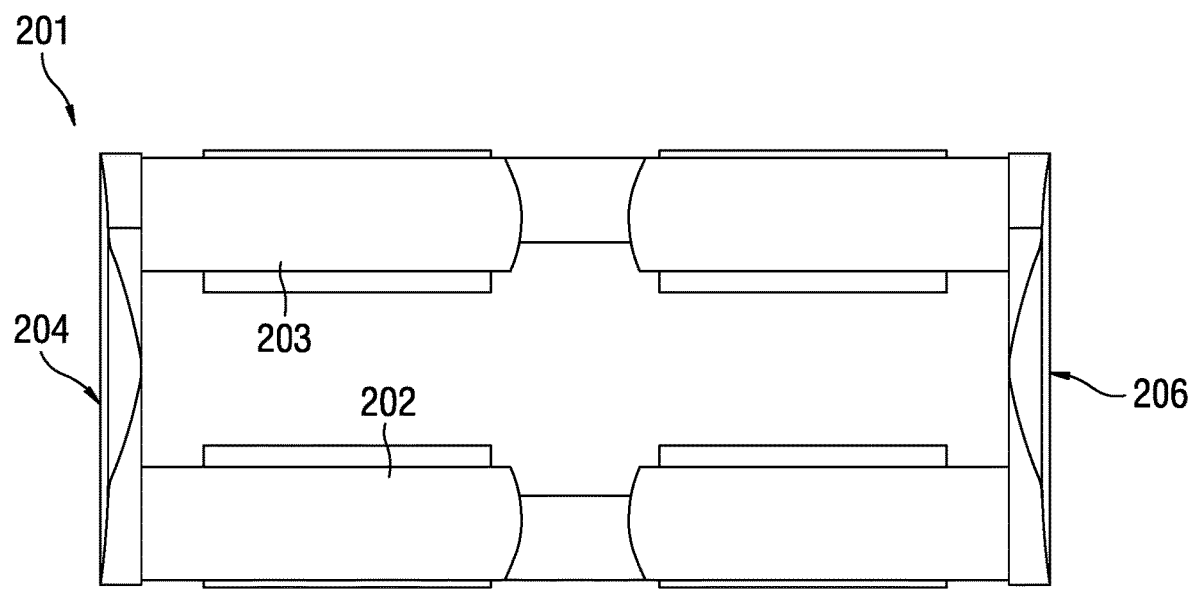
FIG. 3 is another side view of an open pump according to exemplary aspects of the present disclosure.

FIG. 3 is a side view of the open pump of FIG. 2. In FIG. 3 the rotor, central axle 103, and bushings 106 that hold the central axle 103 are omitted for clarity. As can be seen, the structure of the frame 201 in FIG. 2 includes two members 202, 203 that each hold two electromagnetic coils and two endplates 204 and 206 that respectively attach to the ends of the two members 202, 203. However, the frame 201 may also be made as a single piece without departing from the scope of the present disclosure.

Figure 4:
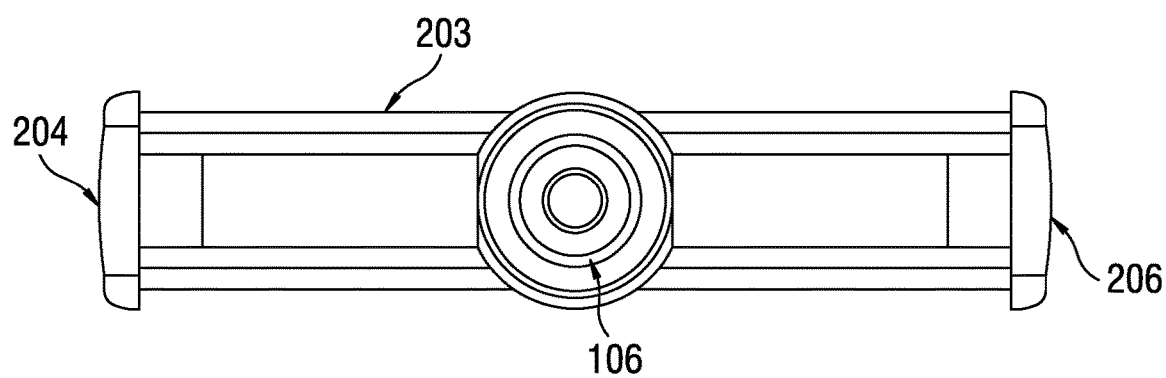
FIG. 4 is a top view of an open pump according to exemplary aspects of the present disclosure.

FIG. 4 is a top view of the open pump of FIGS. 2 and 3. In FIG. 4 the bushing 106, endplates 204, 206, and one of the members 203 are illustrated. As can be seen from this figure, the coils 205 are held in place by the member 203 in a recess created for the coils 205 by the side walls of the member 203. Because the side walls of the member 203 curve around the coils 205 no additional retainer is needed to hold the coils 205 in place. However, additional retainers such as a clamp, screw, etc., may also be used in addition to, or instead of the curved sidewalls of the member 203 in order to hold the coils 250 in place. The coils 205 may also be held in place using a resin or adhesive, as one of ordinary skill would recognize. Though not illustrated, the member 202 has substantially the same structure as the member 203.

Figure 5:
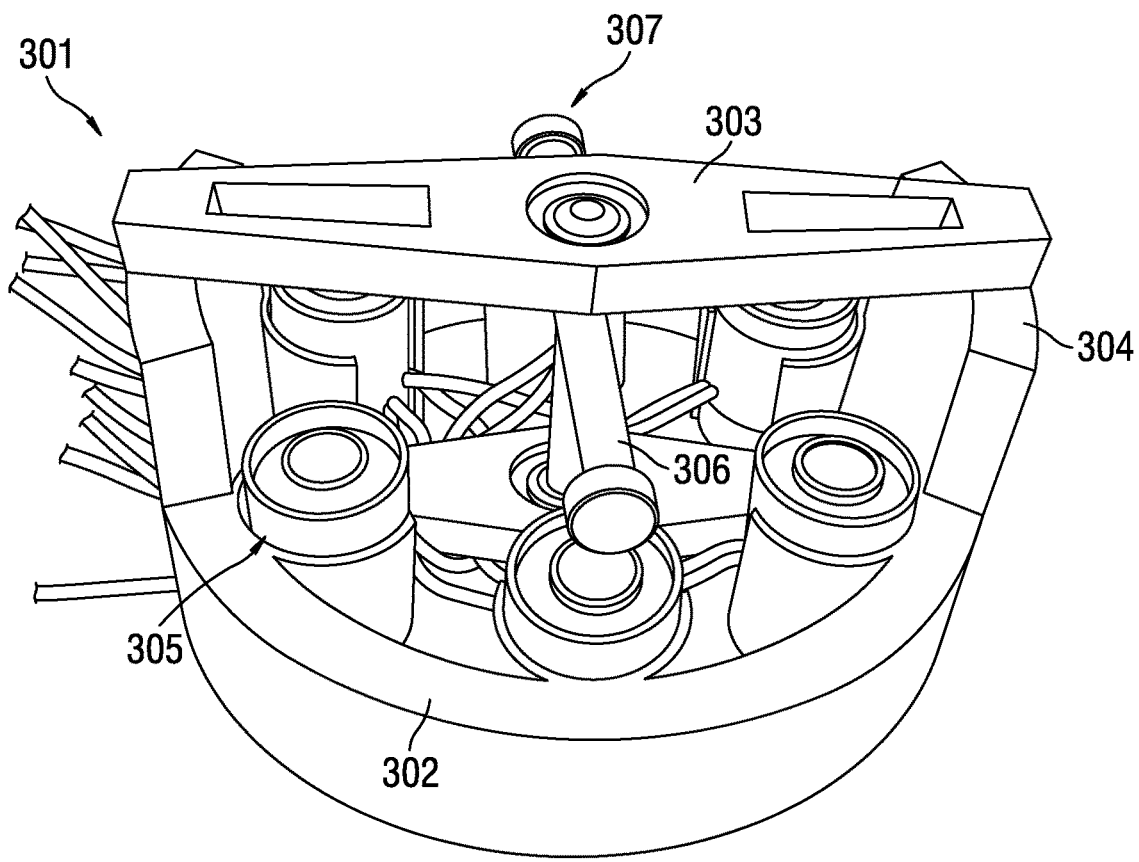
FIG. 5 is a perspective view of an open pump according to exemplary aspects of the present disclosure.

FIG. 5 is a perspective view of an open pump according to exemplary aspects of the present disclosure. The pump includes a frame 301 that includes a cylinder 302 which holds a plurality of electromagnetic coils 305 arrange around the interior circumference thereof. The cylinder 302 includes two supports 304 that support a beam 303 into which a bushing 308 to hold the central axle of the rotor 306 is placed. A similar beam is also affixed to the opposite side of the cylinder 302. The cylinder 302 can be made of a flexible material for minimally invasive implantation, such as an endovascular stent holding rigid support beams 303 and 304. The rotor 306 includes magnets 307 that, in combination with the electromagnetic coils 305, cause the rotor 306 to spin. The rotor can have different shapes than in this schematic drawing, such as in FIG. 1 to optimally propel the blood. The rotor can also be made of magnetic material itself this obviating the need for separate magnets. As can be seen, the electromagnetic coils 305 are arranged perpendicular or minimally oblique to the rotor 306 and parallel to a flow of blood. Though FIG. 5 illustrates 6 coils 305, more or fewer coils 305 may be used depending on application as one of ordinary skill would recognize.

Figure 6:
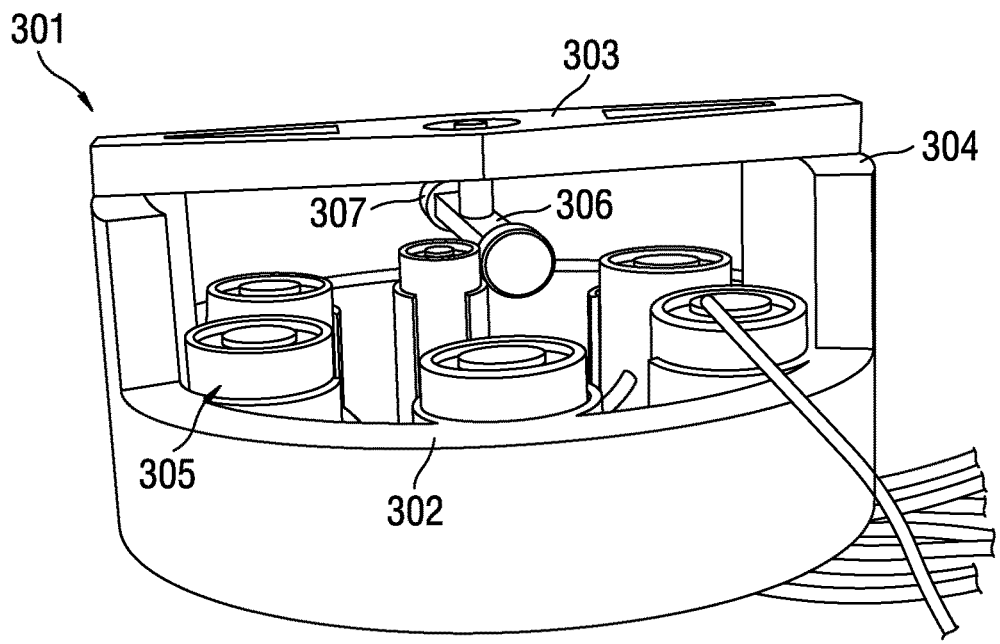
FIG. 6 is a side view of the open pump according to exemplary aspects of the present disclosure.

FIG. 6 is a side view of the open pump of FIG. 5. As can be seen from this view, the rotor 306 is suspended above the cylinder 302 and electromagnetic coils 305 such that the overall structure of the pump remains open and present low resistance to blood flow. The coils 305 may be held in place via a pressure fit in individual cylinders formed around the circumference of the cylinder 302, or may be adhered in place with an adhesive or resin. The coils 305 may also be mechanically held with a retainer, or fastener, such as a clamp. Other methods and structures for holding the coils 305 in place are also possible without departing from the scope of the present disclosure.

Figure 7:
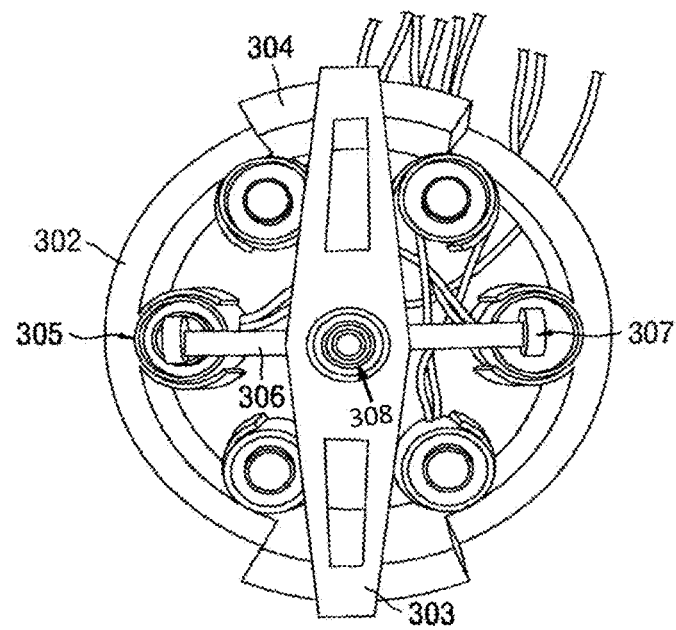
FIG. 7 is a top view of the open pump according to exemplary aspects of the present disclosure.

FIG. 7 is a top view of the pump of FIGS. 5 and 6. This figure illustrates the open design of the pump, which allows blood to flow even when the pump is stopped. The figure also illustrates that the bushing 308 that holds the axle 309 of the rotor 306. As can be appreciated, the bushing 308 may be omitted and the axle 309 may be held in place directly by the frame 301 and a cotter pin at each end of the axle 309.

The pump illustrated in FIGS. 5-7 may be scaled to fit in a human heart and that the electromagnetic coils, which are oriented perpendicularly to the rotor in the direction of blood flow, can be mounted on a vascular stent or a stent graft (not shown). The electromagnetic coils can also be held in position with flexible circular or diagonally oriented metal struts made from a metal, a metal alloy such as Nitinol or a polymer.

Figure 8:
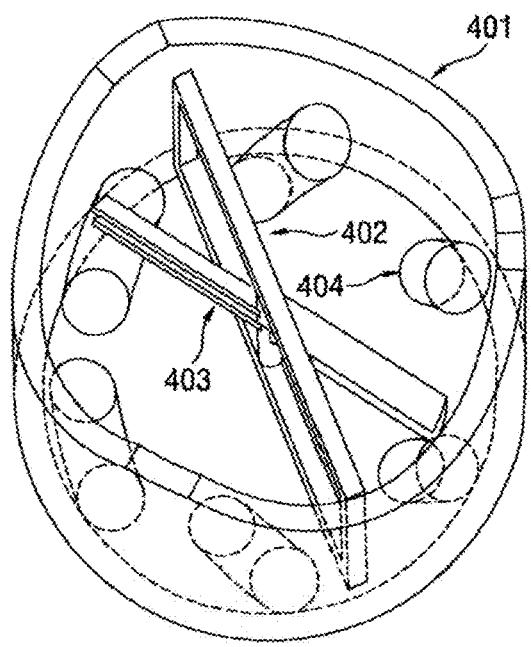
FIG. 8 is a perspective view of an open pump according to exemplary aspects of the present disclosure.

FIG. 8 is a perspective view of an open pump according to exemplary aspects of the present disclosure. The pump in FIG. 8 includes a cylinder 401 in which a frame 402 is installed. The frame 402 holds the central axle of a rotor 403. Along the interior circumference of the cylinder 401 are a plurality of electromagnetic coils 404 that are arranged at a predetermined angle relative to the blood flow. This predetermined angle may be any angle between 0 and 180 degrees, as one of ordinary skill would recognize. As can be appreciated, the cylinder 401 may be replaced with a stent or a stent graft that holds the pump in place in the heart. The frame 402 may also be formed with the cylinder 401 as one piece. 401 shows another exemplary rotor configuration with a "double blade rotor". Other variations are possible without departing from the scope of the present disclosure.

Though the pumps described above have been described individually for the sake of clarity, one of ordinary skill would recognize that the different features described for one pump may be combined with the features of the other pumps without limitation.

Moreover, to the extent that the figures and descriptions herein identify a specific number of electromagnetic coils, such number is merely exemplary since for each pump more, weaker coils may be used, or fewer, stronger coils may be used. The pumps may also be made of any material that is compatible with implantation in living tissue, and part or the entire pump may be coated with a conformal coating in order to protect the pump components.

The descriptions herein have been made with reference to implantation of the inventive pump in a failing heart for the sake of clarity. However, the inventive pump may be used in other applications in which a pump that presents little resistance to flow when stopped is required. Accordingly, the descriptions herein are merely exemplary and do not limit the scope of the present disclosure. Obviously, numerous modifications and variations of the present invention are possible in light of the above teachings. It is therefore to be understood that within the scope of the appended claims, the invention may be practiced otherwise than as specifically described herein.

The invention claimed is:

1. An implantable pump configured to be in series with blood flow from a heart, the pump comprising:
    a frame configured to be implanted in a natural blood path of blood in the heart, including in a ventricular outflow tract of the heart or in place of outlet valves of the heart;
    a central axle disposed within the frame and held by the frame in a position parallel to the blood flow, the central axle being configured to rotate;
    a rotor attached to the central axle and configured to rotate with the central axle in order to pump blood; and
    at least two electromagnetic coils configured to be energized in order to cause the rotor and the central axle to rotate, the at least two electromagnetic coils overlapping the rotor when the implantable pump is viewed from a direction parallel to the blood flow,
    wherein the frame includes at least two members that each span a width of the implantable pump, each of the at least two members having recesses formed by curved side walls that partially wrap around each of the at least two electromagnetic coils to hold the at least two electromagnetic coils.

2. The implantable pump according to claim 1, wherein the frame has at least one opening in a direction of the blood flow to allow the blood to flow without obstruction when the rotor does not rotate.

3. The implantable pump according to claim 1, wherein the at least two electromagnetic coils are positioned radially with respect to a direction of the blood flow.

4. The implantable pump according to claim 1, wherein both of the at least two electromagnetic coils are situated in the frame on a same side of the rotor.

5. The implantable pump according to claim 1, wherein a first of the at least two electromagnetic coils is situated on a first side of the rotor, and a second of the at least two electromagnetic coils is situated on a second side of the rotor that is opposite the first side.

6. The implantable pump according to claim 1 wherein the frame includes a cylindrical member whose opening is positioned in line with the blood flow.

7. The implantable pump according to claim 6, wherein the cylindrical member is a stent or a stent graft.

8. The implantable pump according to claim 1, wherein the central axle is inserted into opposite ends of the frame and held, at each of the opposite ends of the frame, by bushings.

* * * * *